United States Patent
Lodaya et al.

(12)

(10) Patent No.: US 6,184,385 B1
(45) Date of Patent: Feb. 6, 2001

(54) PROCESS FOR THE MANUFACTURE OF A SULFENIMIDE

(75) Inventors: Jayant S. Lodaya, Akron; Donald L. Fields, Jr., Copley, both of OH (US); Raymond T. Parker, Poca; Phillip B. Balderson, Cross Lanes, both of WV (US)

(73) Assignee: Flexsys America L.P., Akron, OH (US)

( * ) Notice: Under 35 U.S.C. 154(b), the term of this patent shall be extended for 0 days.

(21) Appl. No.: 09/292,682

(22) Filed: Apr. 16, 1999

Related U.S. Application Data

(60) Provisional application No. 60/084,825, filed on May 8, 1998.

(51) Int. Cl.[7] ................................................. C07D 417/12

(52) U.S. Cl. ............................................ 548/157; 564/102

(58) Field of Search ............................... 564/102; 548/157

(56) References Cited

U.S. PATENT DOCUMENTS 5,204,481 * 4/1993 Carroll ................................. 548/157
5,286,870 * 2/1994 Sichender ............................ 548/157

* cited by examiner

*Primary Examiner*—Robert Gerstl
(74) *Attorney, Agent, or Firm*—Louis A. Morris

(57) ABSTRACT

A process for the manufacture of a sulfenimide by reacting sulfenamide in slurry with a water immiscible organic solvent with an acid to yield a solvent slurry comprising sulfenimide product. The product is recovered from the solvent slurry by a method comprising the addition of water to the solvent slurry and the isolating of the product by a single filtration step. While water is added to the solvent slurry an azeotrope of solvent and water may be distilled under vacuum until substantially all solvent is separated from product and product becomes part of an aqueous slurry. Alternatively, water may be added to the solvent slurry while the resulting mixture is being agitated, followed by filtering the mixture in the single filtration step for recovery of product from the mixture.

20 Claims, 1 Drawing Sheet

PROCESS FOR THE MANUFACTURE OF A SULFENIMIDE

This application claims priority to the filing date of U.S. Provisional Application 60/084,825, filed May 8, 1998, the disclosure of which is hereby incorporated by reference in its entirety.

FIELD OF THE INVENTION

This invention relates to a process for preparing a sulfenimide from a sulfenamide employing a novel method for recovering the product from the reaction mixture.

BACKGROUND OF THE INVENTION

Santocure® TBSI (N-t-butyl-2-benzothiazole sulfenimide) is a good replacement for secondary amine based sulfenamide accelerators which are under close environmental scrutiny due to potential nitrosoamine generation during the processing and curing of rubber. Santocure® TBSI has a long scorch delay and slow cure rate which mimics the secondary amine based sulfenamide accelerators.

It is known to manufacture Santocure® TBSI from N-t-butyl-2-benzothiazole sulfenamide (Santocure® NS) and gaseous hydrogen chloride with heptane used as the solvent as shown by the following reaction:

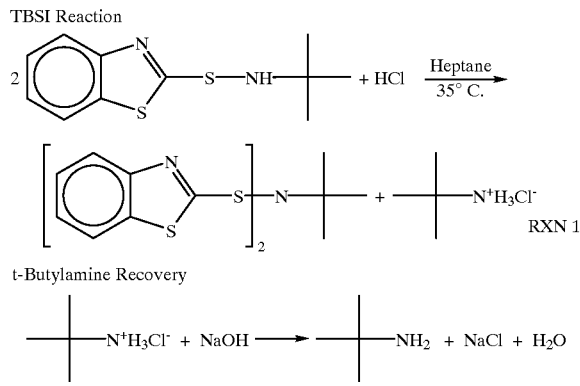

The prior art process involves filtration of heptane slurry to give a crude product which is fully dried and then reslurried in water at 50° C. and then filtered and dried to give a final product. The heptane is recovered by distillation and the heptane still bottoms are incinerated. Thus, this process involves two filtration and two drying steps and recovery of heptane by distillation. This two step filtration/drying process has heretofore been considered to be the only practical means of transferring the Santocure® TBSI from the solvent phase to the aqueous phase.

For example, U.S. Pat. No. 5,204,481 provides a typical description of the known process in Examples 1 and 2. The reactor mixture is first subjected to a vacuum filtration to separate mixed reaction solids from heptane, the solids are washed and dried and the dry mixed solids are slurried in water to dissolve the hydrochloride salt. The product is then isolated by a further vacuum filtration, water washing and drying.

The prior art process does produce Santocure® TBSI in high yields and high assay, but as previously mentioned, it demands two filtration and two drying steps. Overall, the prior art process is complicated and inefficient, thereby creating a long felt but heretofore unfulfilled need for process improvements.

SUMMARY OF THE INVENTION

Accordingly, the present invention comprises a process for the manufacture of a sulfenimide from an sulfenamide. The sulfenamide in slurry with a water immiscible organic solvent is reacted with an acid to yield a solvent slurry comprising the sulfenimide product. The product is recovered from the solvent slurry by a method comprising the addition of water to the solvent slurry and the isolating of the product by a single filtration step.

More detailed embodiments of the invention will be described hereinbelow, particularly with regard to recovery of product from the reaction mixture.

DETAILED DESCRIPTION OF THE INVENTION

Figure 1:
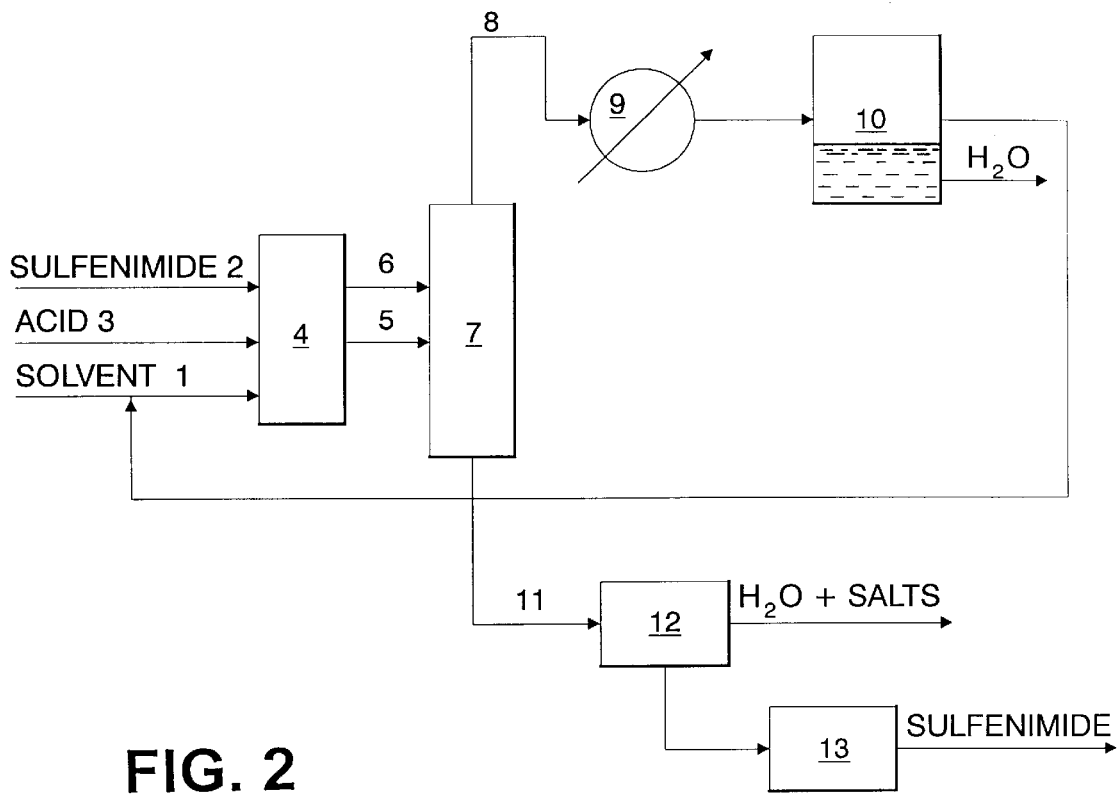
FIG. 1 is a flow diagram of the embodiment of the invention employing an azeotropic distillation.

In its broadest concept, the process of the present invention comprises the addition of water to a water immiscible organic liquid slurry that contains a sulfenimide product resulting from a process where a sulfenamide in the organic water immiscible liquid is reacted with an acid, and recovering the product from the resulting two liquid phase system with only one filtration.

The sulfenimide manufactured by the process of the invention may be sulfenimides of the formula (R1S—)(R2S—)N—R, where R is selected from the group comprising t-butyl, cyclohexyl, or C1–C20 alkyl, and R1 and R2 may be the same or different and are selected from various substituted or unsubstituted heterocycles containing one or more atoms from N,S,O and P, and may be substituted further with C1–C20 alkyl groups or other functional groups. The sulfenamides employed may be of the formula R1S—NH-R. Commonly, the heterocycles will be substituted or unsubstituted benzothiazole.

The acid reactants may be any which will effectively enter into the desired reaction with the sulfenamide which most probably are acids having ionization constants Ka, which are greater than 0.001 at 25° C. Examples include hydrochloric acid, hydrobromic acid, sulfuric acid, chlorobenzoic acid, o-nitrobenzoic acid and the like. Of these acids, hydrochloric acid is preferred. In general, overcharge of acid results in a high percentage of 2,2'-dithiobis(benzothiozole), commonly referred to as MBTS, whereas undercharge of acid helps control MBTS formation.

A preferred solvent is heptane which may be either n-heptane or mixtures of $C_7$ saturated hydrocarbons.

The instant new process eliminates the solvent slurry filtration step and drying of mixed solids step. Thus it results in significant reduction in process time and capital investment in equipment. It also eliminates a solvent distillation step and does not generate solvent still bottoms, resulting in significant savings. It provides a significant yield increase.

In one embodiment, while water is being added to the reaction mixture an azeotrope of solvent and water is being distilled under vacuum until substantially all solvent is separated from the product and the product becomes part of an aqueous slurry. Residual acid may be removed from the solvent slurry by addition of a very small amount of alkaline substance such as caustic or soda ash to neutralize the acid, or, if the acid is gaseous at standard conditions, such removal may be effected by heating the slurry while under a vacuum or by sparging an inert gas through the reaction mixture. The distillation is continued until all the solvent is removed, leaving behind the product in water slurry.

The resulting distillates, organic solvent and water will form two layers. The layers may be easily separated. It has been surprising to find that the recovered organic solvent layer is sufficiently low in water content so as to be suitable for recycle to the reactor.

With regard to the manufacture of Santocure® TBSI from Santocure® NS, employing hydrogen chloride as the acid and heptane as the solvent, the azeotropic distillation is preferably carried out at a temperature of about 50° C. and a vacuum of about 20 to about 25 inches of mercury, A byproduct of the reaction will be an ammonium salt. Sufficient water should be added to the solvent slurry to enable substantially all of the salt to be in solution in the aqueous slurry following distillation of the azeotrope and to enable the aqueous slurry to be readily filtered. The solvent and water removed by distilling of the azeotrope is recovered as two liquid phases and the solvent phase may be recycled for further use in the reaction.

In another embodiment (referred to as "water extraction"), rather than distilling off a solvent/water azeotrope, water is added to the solvent slurry of product while the resulting mixture is being agitated, followed by filtering the mixture in a single filtration step to recover the product from the mixture. It is also preferred in this embodiment to add sufficient water to the solvent slurry to enable substantially all of the salt formed as a reaction byproduct to be in solution in the aqueous slurry and the aqueous slurry to be readily filtered. An alkaline substance may be dissolved in the added water to neutralize excess acid, if present, and raise the pH of the reaction mixture and eliminate degradation of product. The solvent/water filtrate separates into two distinct phases and is physically separated with ease. Recovered solvent may be continuously recycled.

Also with regard to the water extraction embodiment, it was surprising to find that the solvent slurry, which was an emulsion with unclear boundaries between the liquid phases and with product dispersed throughout both phases, became two clearly distinct phases following filtration of the product which were easily separable to obtain solvent suitable for recycle. It was also surprising that the amount of water in the solvent recovered for recycle, in solution and entrained, was sufficiently minor so as not to have a deleterious effect on the reaction.

In both of the above embodiments, and particularly for the manufacture of Santocure® TBSI with heptane as the solvent, filtering of the slurry may be carried out at a temperature of from about 20° C. to about 55° C. The product recovered from the filtration step may be washed with water and dried.

The terms "filter" or "filtration" as used herein refer not only to what is conventionally understood to comprise a filter or the act of filtering, but is also intended to include other means of solids separation such as centrifugation.

The process of the invention may be further illustrated with reference to the attached Figures.

With regard to the first above mentioned embodiment of the invention, in FIG. 1 solvent, sulfenamide and acid, feed streams 1, 2 and 3, respectively, are added to reactor 4. An amount close to a stoichiometric amount of acid is used and sufficient solvent to provide a slurry that can be effectively stirred. In the experiments described in the following examples, a weight ratio of solvent to Santocure® NS used was 5.6, however, other weight ratios can also be employed effectively. The ratio of solvent to sulfenamide may range from about 1 to about 12.

The reaction is typically carried out at about 25° C. to about 35° C. and ambient pressure. Reaction time will typically run from about 45 minutes to about 180 minutes, beginning with the charging of acid to the solvent and sulfenamide.

The solvent slurry from reactor 4 is passed to vessel 7 where water is added as stream 6 and an azeotrope of solvent and water is distilled off as stream 8 under vacuum and appropriate temperature until all solvent is removed from the reaction mixture. The azeotropic mixture is condensed by condenser 9 with the condensate passed to tank 10 in which distinct solvent and water liquid phases will be maintained. For illustrative purposes, the solvent phase is shown to be above the water phase, but, depending on the specific gravity of the solvent, that would not necessarily be the case. The solvent phase may be readily separated and recycled to the reactor where it joins with a small amount of make-up solvent via line 1.

Although FIG. 1 shows the vessel in which azeotropic distillation occurs to be separate, it is understood that the reactor vessel 4 may also be used for distillation purposes instead of employing a separate vessel 7. However, care should be taken to ensure that before the reaction, all the water is removed to preserve largely anhydrous conditions required for the optimum reaction.

Sufficient water should be added to vessel 7 via line 6 to dissolve all water soluble salts present in the slurry. Also, since some of the water will be removed during distillation, this loss of water should be considered in adjusting the amount of water added to dissolve all the sats in the slurry.

Not shown in the figure are optional means that may be employed to remove excess acid such as acid gases like HCl. Such means include heating the solvent slurry while under a vacuum or by sparging an inert gas through the slurry or by addition of a small amount of an alkaline material to neutralize the acid.

The aqueous slurry from vessel 7 is passed via line 11 to filter 12. The filter mechanism employed may comprise any available filter appropriate for the particular slurry. The filtrate will comprise a solution of the ammonium salt that can be treated using an alkaline material such as sodium hydroxide to produce a free amine which can be reused for other applications. For example, in the case of the manufacture of Santocure® TBSI as described above, t-butylammonium hydrochloride is formed as byproduct which can be reacted with sodium hydroxide to produce t-butylamine which can be recovered by distillation and then reused either for the manufacture of Santocure® NS or for other applications.

The filtered solid material from filter 12 will comprise sulfenimide product which may be water washed and dried via means 13 to obtain final product.

Figure 2:
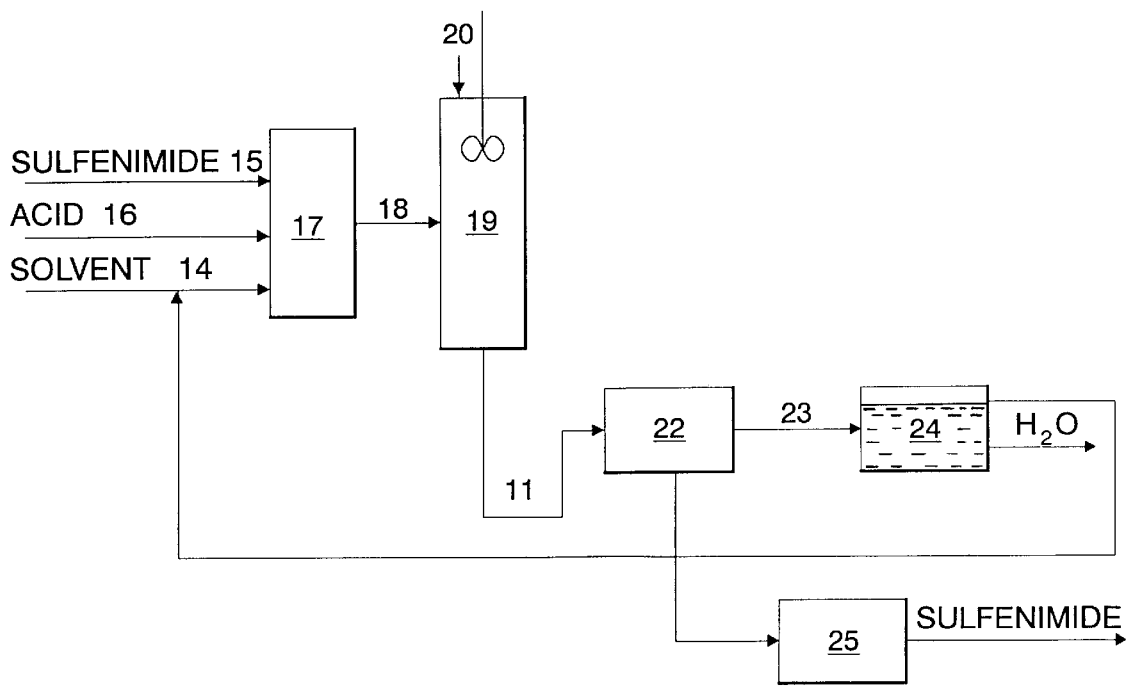
FIG. 2 is a flow diagram of the embodiment of the invention referred to as "water extraction".

With regard to the above mentioned second embodiment of the invention, in FIG. 2 the reaction occurs in reactor 17 with solvent, sulfenamide and acid streams 14, 15 and 16, precisely as in the first embodiment. However, the solvent slurry comprising the reactor slurry is passed via line 18 to vessel 19 where, rather than distillation being carried out, sufficient water is added via line 20 with agitation to dissolve all salts from the reaction mixture. An alkaline substance may also be added to vessel 19 via line 20 or be dissolved in the added water to eliminate excess acid and raise the pH of the reaction mixture.

The slurry from vessel 19 may be passed via line 21 directly to filter 22 which may be the same as or similar to filter 12 of FIG. 1. The filtrate is passed via line 23 to vessel 24 in which distinct solvent and water liquid phases will be maintained. For illustrative purposes, the solvent phase is shown to be above the water phase, but, depending on the specific gravity of the solvent, that would not necessarily be the case. The solvent phase may be readily separated and recycled to the reactor where it joins with a small amount of make-up solvent via line 14. The water phase will comprise a solution of an ammonium salt that can be treated using an alkaline material such as sodium hydroxide to produce an amine that may be recovered.

The filtered solid material from filter 22 will comprise sulfenimide product which may be water washed and dried via means 25 to obtain final product.

completion of removal of heptane could be verified either by drop in head temperature or rise in the reactor temperature or by the fact that no more distillate was being collected. During the distillation step Santocure® TBSI transferred cleanly and neatly to the aqueous phase. The slurry was then vacuum filtered hot (45–50° C.) through a buchner funnel and the product was washed with 50° C. water (2 times 75 mL each). The product was dried in a dietert (forced air oven) at 50° C. to a constant weight and analyzed.

The following table summarizes the results for the lab runs. The yields using the instant process would be higher than the process of the examples of U.S. Pat. No. 5,204,481 where there would be a loss of material due to the solubility of product in heptane that ends up in the filtrate. Also the handling losses would be lower in the instant process compared to the examples of U.S. Pat. No. 5,204,481 since the instant process involves only one filtration and one drying step and not two.

TABLE 1

| No. | Santocure ® TBSI wt % | Perkacit ® MBTS wt % | Santocure ® NS wt % | HCl gms. Charged | m.p. ° C. | % Yield Assuming isolated solids as TBSI |
|---|---|---|---|---|---|---|
| 1 | 94.3% | 1.8% | 3.9% | — | 125–134 | — |
| 2 | 92.4% | 2.3% | 5.3% | 5.5 | 122–136 | 94.2 |
| 3 | 90.2% | 4.1% | 0.6% | 5.8 | 126–136 | 95.1 |

The present invention can be more clearly illustrated by the following non-limiting examples.

EXAMPLES

General: In a typical preparation, a 1500 ml resin kettle equipped with mechanical stirrer, thermocouple, gas dispersion tube and a heating mantle was charged with finely pulverized Santocure®NS (71.5 g, 0.3 moles) and anhydrous heptane (402 g). The mixture was stirred at 25 to 35° C. and HCl (5.5 to 5.8 g) gas was added subsurface over a period of 1.25 to 2 hrs. After completion of HCl addition and 10 to 20 minute digestion period, vacuum was applied (20 to 22 inches of mercury) to remove any residual HCl present in the slurry (it may be helpful to add a very small amount of basic material such as caustic or soda ash to neutralize any residual HCl before heating the reaction mixture). The mixture was then heated to 50 □C, and while it was being heated, water (440 g) was kept ready in the addition funnel. During distillation the reactor lid was also heated and every part was well insulated for an effective temperature control. About 50 to 100 ml water was added initially to provide water to the system for effective azeotrope formation.

Heptane forms an azeotrope with water. Once a constant stream of distillate was being collected, the rest of the water was added at about the same rate that was being distilled over. One can add all the water in one shot if there is enough space in the vessel, or by adding water slowly while removing heptane/water azeotrope, one can avoid need for a larger vessel. The heptane/water distillate formed two layers and could be separated easily and the heptane recycled. Analysis of the heptane layer revealed that it contained a surprisingly very small amount of water (30 to 50 ppm). The heptane could therefore be recycled without the reaction being adversely affected.

Once almost all the heptane was removed, the reactor had essentially all the product and salts in water slurry. The Note/Explanation for Each Experiment in Example 1

Experiment No.1: A larger batch of Santocure® TBSI than what is described above was made using the procedure described above. Then a portion of the slurry was worked up using this new process. Hence yields and HCl charges are not mentioned.

Experiments Nos. 2 and 3: Recycled heptane was used in these batches. The heptane obtained was from the distillate of the other similar batches. The amount of HCl charge has an effect on the formation of MBTS and unreacted Santocure® NS. The amount of water in the system during reaction also has a significant effect on the product assay. Therefore, anhydrous conditions are recommended during the reaction.

It was successfully demonstrated that the proposed process modification involving distillation to remove heptane instead of filtration and drying steps works very well. In the prior art process there would be a loss of solids in the heptane filtrate. There would be no loss of these solids in the instant process, so potentially there would be an increase in yield. This process modification offers tremendous savings potential because of a reduction in requirements for capital equipment (no separate still for heptane distillation and no still bottoms for disposal), higher yields, reduction in total process time, etc.

It was also demonstrated that recycle of heptane is possible (performed two recycles). Overall, the new process offers significant potential for savings and ease of operation.

Example 2

This example illustrates the embodiment of the invention employing water extraction.

Santocure® TBSI was prepared from the following reactor charge:

| | |
|---|---|
| Santocure ® NS pellets | 121.8 grams |
| n-heptane (recycle) | 684 grams |
| HCl gas | 10.3 grams |

HCl gas was fed at a reaction temperature maintained by a water bath at 35° C. over 81 minutes. By forty minutes into the HCl feed a light colored and smooth slurry was obtained with no pellets left. HCl feed was ended and the bottom of the reactor was moved to an extraction set-up which was a reactor top fitted with agitator impellers, including one on the bottom of the reactor run at a rotational speed of 500 rpm.

1000 cc of tap water containing 2.5 grams of technical soda ash was added to the reactor mixture and the mixture was heated to 50° C. and held at that temperature for 30 minutes. The mixture was then cooled to 22° C. using a flowing water bath. The mixture was then filtered through a 40–60 micron sintered glass filter. The resultant cake was then washed with 1000 cc of 45° C. water and the cake then removed and dried overnight in a 65° C. oven. The heptane-water layers were separated by use of a separatory funnel. Separation of the two layers was almost instantaneous. Yield of dried Santocure® TBSI was 98.4 grams or 95.4% of theory.

The instant new process in both of its above embodiments offers tremendous savings potential such as less capital in equipment, higher yields, reduction in total process time, no separate still for solvent distillation and no still bottoms to cause concern. Overall the new process offers significant potential for savings and ease of operation.

We claim:

1. A process for the manufacture of a sulfenimide by reacting sulfenamide in slurry with a water immiscible organic solvent with close to a stoichiometric amount of an acid to yield a solvent slurry comprising sulfenimide product, removing residual acid from said solvent slurry, said product being recovered from said solvent slurry by a method comprising the addition of water to said solvent slurry and the isolating of said produce by a single filtration stop, said sulfenamide having the formula R1S—NH–R where R is selected from the group comprising—t-butyl,cyclohexyl, or C1–C20 alkyl, and R1 is selected from substituted or unsubstituted heterocycles containing one or more atoms from N,S,O and P, and said heterocycles may be substituted with C1–C20 alkyl groups or other functional groups, said sulfenimide being of the formula (R1S—)(R2S—)N—R where R2 is selected from the same group as R1 and may be the same or different as R1, and said acid having an ionization constant, Ka, which is greater than 0.001 at 25° C.

2. The process of claim 1 wherein while water is added to said solvent slurry an azeotrope of solvent and water is distilled under vacuum until substantially all solvent is separated from product and product becomes part of an aqueous slurry, said aqueous slurry being filtered in said single filtration step for recovery of product from said aqueous slurry.

3. The process of claim 2 wherein an ammonium salt is formed as a reaction byproduct and sufficient water is added to said solvent slurry to enable substantially all of said salt to be in solution in said aqueous slurry following distillation of said azeotrope and said aqueous slurry to be readily filtered.

4. The process of claim 2 wherein the solvent and water removed by said distilling of said azeotrope is recovered as two liquid phases and the solvent phase is recycled for use in the reaction.

5. The process of claim 1 wherein residual acid is removed from the reaction mixture by addition of an alkaline substance to neutralize said acid.

6. The process of claim 1 wherein residual acid in the form of an acid gas is removed from the reaction mixture by applying a vacuum to said reaction mixture or by sparging an inert gas through said reaction mixture.

7. The process of claim 1 wherein water is added to said solvent slurry while the resulting mixture is being agitated, followed by filtering said mixture in said single filtration step for recovery of product from said mixture.

8. The process of claim 7 wherein an ammonium salt is formed as a reaction byproduct and sufficient water is added to said solvent slurry to enable substantially all of said salt to be in aqueous solution in a water phase and for said slurry to be readily filtered.

9. The process of claim 7 wherein the filtrate is recovered as solvent and aqueous liquid phases and the solvent phase is recycled for use in the reaction.

10. The process of claim 1 wherein product recovered from said single filtration step is washed with water and dried.

11. The process of claim 1 wherein said heterocycles are substituted or unsubstituted benzothiazole.

12. The process of claim 1 wherein said acid comprises HCl.

13. The process of claim 1 wherein said organic solvent comprises one or more $C_5$–$C_{20}$ saturated hydrocarbons.

14. The process of claim 13 wherein said organic solvent comprises a heptane.

15. The process of claim 1 wherein the filtrate from said single filtration step comprises an aqueous solution of a reaction byproduct comprising an ammonium salt which is treated using an alkaline material to produce an amine that is recovered for use in the manufacture of sulfenamide reactant or for use in other applications.

16. A process for the manufacture of N-t-butyl-2-benzothiazole sulfenimide by reacting N-t-butyl-2-abenzothiazole sulfenamide in slurry with heptane with close to a stoichiometric amount of HCl to yield a heptane slurry comprising N-t-butyl-2-benzothiazole sulfenimide product, removing residual HCl, if any, said product being recovered from said heptane slurry by a method comprising the addition of water to said solvent slurry and the isolating of said product by a single filtration step.

17. The process of claim 16 wherein said single filtration step is carried out at from about 20° C. to about 55° C.

18. The process of claim 16 wherein water is added to said heptane slurry while an azeotrope of heptane and water is being distilled under vacuum until substantially all heptane is separated from product and product becomes part of an aqueous slurry with ammonium salt comprising a byproduct of the reaction being dissolved in the water, the amount of water added to said heptane slurry being sufficient to enable substantially all of the salts in said heptane slurry to be dissolved in said aqueous slurry and said aqueous slurry to be readily filtered, said azeotrope being condensed to form separate aqueous and heptane phases from which heptane may be recovered for recycle to the reactor, said aqueous slurry being filtered in said single filtration step for recovery of product from said aqueous slurry, sodium hydroxide being added to the salt solution comprising the filtrate to produce t-butylamine from the ammonium salt which is recovered for use in the manufacture of N-t-butyl-2-benzothiazole sulfenamide or for use in other applications.

19. The process of claim 18 wherein said vacuum distilling of azeotrope is carried out at about 50° C. and a vacuum of about 20 to about 25 inches of mercury.

20. The process of claim 16 wherein water is added to said heptane slurry while the resulting mixture is being agitated, followed by filtering said mixture in said single filtration step for recovery of product from said mixture, sufficient water being added to said heptane slurry to enable substantially all of the salt formed in the reaction to be in aqueous solution and the slurry to be readily filtered, the filtrate from said filtration step comprising separate phases of water and heptane, the heptane being recovered from said filtrate and recycled to the reactor, adding sodium hydroxide to the ammonium salt solution comprising the filtrate to produce t-butylamine which is recovered for use in the manufacture of N-t-butyl-2-benzothiazole sulfenamide or for use in other applications.

* * * * *